United States Patent [19]

Alaimo et al.

[11] 4,336,199
[45] Jun. 22, 1982

[54] 5-(2,4-DICHLOROPHENYL)-3-FURANCARBOXALDEHYDE-O-[(METHYLAMINO)CARBONYL]OXIME

[75] Inventors: Robert J. Alaimo; Joseph E. Gray, both of Norwich, N.Y.

[73] Assignee: Morton-Norwich Products, Inc., Norwich, N.Y.

[21] Appl. No.: 281,994

[22] Filed: Jul. 10, 1981

[51] Int. Cl.³ ............................................. C07D 307/54
[52] U.S. Cl. ..................................... 549/496; 424/285
[58] Field of Search ...................................... 260/347.3

[56] References Cited

U.S. PATENT DOCUMENTS 3,063,823 11/1962 Kühle et al. .................... 564/255 X
3,217,037 11/1965 Payne et al. ......................... 564/255
3,957,867 5/1976 Bukowick .................... 260/347.3 X

*Primary Examiner*—Richard Raymond
*Attorney, Agent, or Firm*—Anthony J. Franze

[57] ABSTRACT

The compound 5-(2,4-dichlorophenyl)-2-furancarboxaldehyde-O-[(methylamino)carbonyl]oxime is useful as an antifungal agent.

1 Claim, No Drawings

5-(2,4-DICHLOROPHENYL)-3-FURANCARBOXALDEHYDE-O-[(METHYLAMINO)CARBONYL]OXIME

This invention is concerned with the compound 5-(2,4-dichlorophenyl)-2-furancarboxaldehyde-O-[(methylamino)carbonyl]oxime. This compound possesses antifungal activity. In particular it is inimical to the growth of *Microsporum canis* in the commonly employed in vitro technique for determining antifungal activity at a concentration of about 250 mcg of compound per milliliter of test media. Furthermore, it is also efficacious in the in vivo treatment of fungal infections. Thus, when administered per os as an aqueous suspension at a dose of about 35 mg/kg t.i.d. for five days post-infection to mice in which *Torulopsis glabrata* infection had been induced by the IV administration in physiologic saline of 2,000,000 cells of *T. glabrata*, a 40% reduction in viable yeast cells present in spleen and heart tissue was effected.

The compound of this invention can be readily combined in known carriers, adjuvants and vehicles to provide compositions adapted to control or eradicate fungal growth.

The presently preferred method for the preparation of the compound of this invention is here below set forth.

A. 5-(2,4-Dichlorophenyl)-2-furancarboxaldehyde Oxime

A mixture of 5-(2,4-dichlorophenyl)-2-furancarboxaldehyde (635 g, 2.63 moles), anhydrous sodium acetate (432 g, 5.26 moles), hydroxylamine hydrochloride (366 g, 5.26 moles), SDA #30 (9184 ml) and water (918 ml), was refluxed for 5⅛ hours and allowed to stand overnight. The mixture was added to ice/$H_2O$ (42 liters), stirred 1 hour and filtered. The grayish-tan solid was washed with water (10 liters), filtered and dried at 65° to 660 g (98%).

An analytical sample was prepared by recrystallizing a sample twice from isopropyl alcohol (ca. 25 ml/g) and drying in the vacuum oven (ca. 90°) to give a white solid, m.p. 182°–83° (corrected, MEL.TEMP.).

Anal. Calcd. for $C_{11}H_7Cl_2NO_2$: C, 51.59; H, 2.76; N, 5.47; Cl, 27.69. Found: C, 51.78; H, 2.76; N, 5.45; Cl, 28.10; 28.01.

B. 5-(2,4-Dichlorophenyl)-2-furancarboxaldehyde-O-[(methylamino)-carbonyl]oxime 5-(2,4-Dichlorophenyl)furylformaldoxime (1.5 g, 0.006 mole) and 300 ml of anhydrous ether was cooled to 5°. The mixture was stirred and treated with methyl isocyanate (2 ml, 0.034 mole). The addition rate was adjusted to maintain a 10° reaction temperature. The reaction mixture was stirred for 15 minutes at 5°. The precipitate was filtered and layered with cold ether; 1.6 g (87%).

An analytical sample was prepared by one recrystallization from chloroform.

Anal. Calcd. for $C_{13}H_{10}Cl_2N_2O_3$: C, 49.86; H, 3.22; N, 8.95. Found: C, 49.71; H, 3.6; N, 8.66.

What is claimed is:

1. The compound 5-(2,4-dichlorophenyl)-2-furancarboxaldehyde-O-[(methylamino)carbonyl]oxime.